(12) United States Patent
Jabbari (10) Patent No.: US 11,058,797 B2
(45) Date of Patent: *Jul. 13, 2021

(54) COMPOSITIONS AND LAYERED STRUCTURES FORMED THEREWITH FOR REGENERATION OF ARTICULAR CARTILAGE

(71) Applicant: University of South Carolina, Columbia, SC (US)

(72) Inventor: Esmaiel Jabbari, Bethesda, MD (US)

(73) Assignee: University of South Carolina, Columbia, SC (US)

( * ) Notice: Subject to any disclaimer, the term of this patent is extended or adjusted under 35 U.S.C. 154(b) by 557 days.

This patent is subject to a terminal disclaimer.

(21) Appl. No.: 15/897,363

(22) Filed: Feb. 15, 2018

(65) Prior Publication Data

US 2018/0256780 A1 Sep. 13, 2018

Related U.S. Application Data

(60) Provisional application No. 62/468,539, filed on Mar. 8, 2017.

(51) Int. Cl.
*A61L 27/26* (2006.01)
*A61L 27/52* (2006.01)
(Continued)

(52) U.S. Cl.
CPC ............ *A61L 27/26* (2013.01); *A61K 9/0024* (2013.01); *A61K 9/5031* (2013.01); *A61K 38/18* (2013.01);
(Continued)

(58) Field of Classification Search
CPC ......... A61L 27/26; A61L 27/52; A61K 47/58; A61K 9/0024; A61K 38/18
See application file for complete search history.

(56) References Cited

U.S. PATENT DOCUMENTS 6,884,432 B2 4/2005 Yaszemski et al.
7,642,300 B2 1/2010 Yaszemski et al.
(Continued)

OTHER PUBLICATIONS

Karimi et al. "A developmentally inspired combined mechanical and biochemical signaling approach on zonal lineage commitment of mesenchymal stem cells in articular cartilage regeneration" Integr. Biol., 2015, 7, 112-127. (Year: 2015).*

(Continued)

*Primary Examiner* — Kevin K Hill
*Assistant Examiner* — James Joseph Graber
(74) *Attorney, Agent, or Firm* — Dority & Manning, PA (57) ABSTRACT

Compositions and implants for articular cartilage repair or regeneration are described. The compositions are hydrogel-based compositions that can incorporate signaling molecules for cartilage repair. The compositions include microcapsules having predetermined erosion profiles that are loaded with nanogels having predetermined sustained release profiles for signaling molecules conjugated to the nanogels. A plurality of compositions, each carrying different signaling molecules, can be layered to form a multi-layered implant, with each layer sequentially releasing the encapsulated signaling molecules over a predetermined period of time. The compositions can carry additional components to encourage tissue generation such as stem cells and extracellular matrix (ECM) components.

10 Claims, 8 Drawing Sheets

(51) Int. Cl.
| | |
|---|---|
| A61K 47/58 | (2017.01) |
| A61K 38/18 | (2006.01) |
| A61L 27/58 | (2006.01) |
| A61K 47/69 | (2017.01) |
| A61K 47/60 | (2017.01) |
| A61K 47/59 | (2017.01) |
| A61K 9/50 | (2006.01) |
| A61K 38/30 | (2006.01) |
| A61L 27/54 | (2006.01) |
| A61K 9/00 | (2006.01) |

(52) U.S. Cl.
CPC ...... *A61K 38/1841* (2013.01); *A61K 38/1875* (2013.01); *A61K 38/30* (2013.01); *A61K 47/58* (2017.08); *A61K 47/593* (2017.08); *A61K 47/60* (2017.08); *A61K 47/6903* (2017.08); *A61K 47/6937* (2017.08); *A61L 27/52* (2013.01); *A61L 27/54* (2013.01); *A61L 27/58* (2013.01); *A61L 2300/252* (2013.01); *A61L 2300/414* (2013.01); *A61L 2300/602* (2013.01); *A61L 2300/622* (2013.01); *A61L 2300/80* (2013.01); *A61L 2400/06* (2013.01); *A61L 2400/12* (2013.01); *A61L 2430/06* (2013.01)

(56) References Cited

U.S. PATENT DOCUMENTS

| | | |
|---|---|---|
| 9,101,654 B2 | 8/2015 | Jabbari |
| 9,314,549 B2 | 4/2016 | Jabbari |
| 9,808,555 B2 | 11/2017 | Jabbari |
| 2007/0043202 A1 | 2/2007 | Yaszemski et al. |
| 2008/0206308 A1 | 8/2008 | Jabbari et al. |
| 2010/0084784 A1 | 4/2010 | Jabbari |
| 2010/0086607 A1 | 4/2010 | Jabbari |
| 2010/0322979 A1 | 12/2010 | Jabbari |
| 2010/0327494 A1 | 12/2010 | Jabbari |
| 2012/0226295 A1 | 9/2012 | Jabbari |
| 2014/0349367 A1 | 11/2014 | Jabbari |
| 2015/0175972 A1 | 6/2015 | Jabbari |
| 2018/0250438 A1 | 9/2018 | Jabbari |

OTHER PUBLICATIONS

Mak et al. "Indian hedgehog signals independently of PTHrP to promote chondrocyte hypertrophy" Development 200, 135(11): 1947-1956. (Year: 2008).*

Barati et al. "Spatiotemporal release of BMP-2 and VEGF enhances osteogenic and vasculogenic differentiation of human mesenchymal stem cells and endothelial colony-forming cells co-encapsulated in a patterned hydrogel", Journal of Controlled Release 223 (2015) 126-136. (Year: 2015).*

Lee et al. "Production of nanoparticles-in-microparticles by a double emulsion method: A comprehensive study", European Journal of Pharmaceutics and Biopharmaceutics 83 (2013) 168-173. (Year: 2013).*

Srinivasan et al. "Injectable perlecan domain 1-hyaluronan microgels potentiate the cartilage repair effect of BMP2 in a murine model of early osteoarthritis", Biomed. Mater. 7 (2012) 024109, pp. 1-11. (Year: 2012).*

Makadia et al. "Poly Lactic-co-Glycolic Acid (PLGA) as Biodegradable Controlled Drug Delivery Carrier", Polymers (Basel), Sep. 1, 2011; 3(3): 1377-1397. (Year: 2011).*

Nichol et al. "Cell-laden microengineered gelatin methacrylate hydrogels", Biomaterials 31 (2010) 5536-5544. (Year: 2010).*

Nguyen et al. "Engineering articular cartilage with spatially-varying matrix composition and mechanical properties from a single stem cell population using a multi-layered hydrogel" Biomaterials 32 (2011) 6946-6952. (Year: 2011).*

Beck et al. "Approaching the compressive modulus of articular cartilage with a decellularized cartilage-based hydrogel", Acta Biomaterialia 38, Apr. 2016, 94-105. (Year: 2016).*

Holland et al. "Dual growth factor delivery from degradable oligo(poly(ethylene glycol) fumarate) hydrogel scaffolds for cartilage tissue engineering", Journal of Controlled Release 101 (2005) 111-125. (Year: 2005).*

Jayasuriya et al. "The influence of tissue microenvironment on stem cell-based cartilage repair" Ann N Y Acad Sci. Nov. 2016, 1383(1): 21-33. (Year: 2016).*

Anderson, et al. "Post-Traumatic Osteoarthritis: Improved Understanding and Opportunities for Early Intervention." J. Orthop. Res. 29(6): (2011), pp. 802-809.

Andrades, et al., "Induction of superficial zone protein (SZP)/lubricin/PRG 4 in muscle-derived mesenchymal stem/progenitor cells by transforming growth factor-beta 1 and bone morphogenetic protein-7," Arthritis Res. Ther. 14(2): (2012), R72.

Annabi et al., "25th Anniversary Article: Rational Design and Applications of Hydrogels in Regenerative Medicine," Advanced Materials, 26 (2014), pp. 85-124.

Aoyama et al., "Keratin Nanofiber Scaffold for Vascular Graft" (Abstract Only), Tissue Engineering Part A, 21 (2015), p. S244.

Arai et al., "Amino acid sequence of feather keratin from fowl," European Journal of Biochemistry, 132 (1983), pp. 506-507.

Audouin, et al., "Surface-initiated RAFT polymerization of NIPAM from monolithic macroporous polyHIPE," European Polymer Journal 49(5): pp. 1073-1079 (2013).

Balaji et al., "Characterization of keratincollagen 3D scaffold for biomedical applications," Polymers for Advanced Technologies, 23 (2012), pp. 500-507.

Barati et al., "Effect of Organic Acids on Calcium Phosphate Nucleation and Osteogenic Differentiation of Human Mesenchymal Stem Cells on Peptide Functionalized Nanofibers," Langmuir, 31 (2015), pp. 5130-5140.

Barati et al., "Time dependence of material properties of polyethylene glycol hydrogels chain extended with short hydroxy acid segments," Polymer, 55 (2014), pp. 3894-3904.

Barone et al., "Thermally processed keratin films," Journal of Applied Polymer Science, 97 (2005), pp. 1644-1651.

Bernardes et al., "Facile conversion of cysteine and alkyl cysteines to dehydroalanine on protein surfaces: versatile and switchable access to functionalized proteins," Journal of the American Chemical Society, 130 (2008), pp. 5052-5053.

Bhardwaj et al., "Silk fibroin-keratin based 3D scaffolds as a dermal substitute for skin tissue engineering," Integrative Biology, 7 (2015), pp. 53-63.

Burnett et al., "Hemostatic properties and the role of cell receptor recognition in human hair keratin protein hydrogels," Biomaterials, 34 (2013), pp. 2632-2640.

Chalker et al., "Chemical modification of proteins at cysteine: opportunities in chemistry and biology," Chemistry—An Asian Journal, 4 (2009), pp. 630-640.

Chan et al., "Crosslinking of collagen scaffolds promotes blood and lymphatic vascular stability," Journal of Biomedical Materials Research Part A. 102 (2014), pp. 3186-3195.

Chen et al., "A Universal and Facile Approach for the Formation of a Protein Hydrogel for 3D Cell Encapsulation," Advanced Functional Materials, 25 (2015), pp. 6189-6198.

Chen et al., "Engineering Vascularized Tissue Constructs using an Injectable Cell-laden Collagen Hydrogel" (Abstract Only), Tissue Engineering Part A, 21 (2015), S102.

Dawson et al., "Biomaterials for stem cell differentiation," Advanced Drug Delivery Reviews, 60 (2008), pp. 215-228.

Dong et al., "Injectable Hybrid Hydrogel for Mesenchymal Stem Cell Delivery, from PEG-based Multifunctional Hyperbranched Polymers" (Abstract Only), Tissue Engineering Part A, 21 (2015), S298-S289.

Eastoe, "The amino acid composition of mammalian collagen and gelatin," Biochemical Journal, 61 (1955), p. 589.

Evans, et al., "Use of Genetically Modified Muscle and Fat Grafts to Repair Defects in Bone and Cartilage," Eur. Cells Mater. 18 (2009), pp. 96-111.

(56) References Cited

OTHER PUBLICATIONS

Falah, et al., "Treatment of articular cartilage lesions of the knee." International Orthopaedics, 34(5) (2010), pp. 621-630.
Ferlin et al., "Development of a Dynamic Stem Cell Culture Platform for Mesenchymal Stem Cell Adhesion and Evaluation," Molecular Pharmaceutics, 11 (2014), pp. 2172-2181.
Fraser et al., Keratins: their composition, structure, and biosynthesis: Charles C. Thomas, (1972).
Fukumoto, et al., "Combined effects of insulin-like growth factor-1 and transforming growth factor-β 1 on periosteal mesenchymal cells during chondrogenesis in vitro," Osteoarthritis Cartilage 11(1) (2003), pp. 55-64.
Golub et al., "The Role of Alkaline Phosphatase in Cartilage Mineralization," Bone and Mineral, 17 (1992), pp. 273-278.
Gorman, "Materials Take Wing: What to do with 4 billion pounds of feathers?", Science News, 161 (2002), p. 120.
Grogan, et al., "Zone-Specific Gene Expression Patterns in Articular Cartilage," Arthritis Rheum, 65(2) (2013), pp. 418-428.
Guo et al., "In vitro generation of an osteochondral construct using injectable hydrogel composites encapsulating rabbit marrow mesenchymal stem cells," Biomaterials, 30 (2009), pp. 2741-2752.
Han et al., "Alkylation of human hair keratin for tunable hydrogel erosion and drug delivery in tissue engineering applications," Acta Biomaterialia, 23 (2015), pp. 201-213.
Haralson et al., "Extracellular matrix: A practical approach," Annales de Biologie Clinique, (1996), pp. 383-384.
He et al., "Effect of grafting RGD and BMP-2 protein-derived peptides to a hydrogel substrate on osteogenic differentiation of marrow stromal cells," Langmuir, 24 (2008), pp. 12508-12516.
Hoffman, "Hydrogels for biomedical applications," Advanced Drug Delivery Reviews, 64 (2012), pp. 18-23.
Jayathilakan et al., "Utilization of byproducts and waste materials from meat, poultry and fish processing industries: a review," Journal of Food Science and Technology, 49 (2012), pp. 278-293.
Kakkar et al., "Extraction and characterization of keratin from bovine hoof: A potential material for biomedical applications," Springerplus, 3 (2014), p. 596.
Karimi et al., "A developmentally inspired combined mechanical and biochemical signaling approach on zonal lineage commitment of mesenchymal stem cells in articular cartilage regeneration," Integrative Biology, 7 (2015), pp. 112-127.
Kelly et al., "How to study proteins by circular dichroism," Biochimica et Biophysica Acta (BBA)-Proteins and Proteomics, 1751 (2005), pp. 119-139.
Klein, et al., "Depth-dependent biomechanical and biochemical properties of fetal, newborn, and tissue-engineered articular cartilage," Journal Biomech. 40(1) (2007), pp. 182-190.
Kwon et al., "In vivo osteogenic differentiation of human turbinate mesenchymal stem cells in an injectable in situ-forming hydrogel," Biomaterials, 35 (2014), pp. 5337-5346.
Lam, et al., "Osteochondral defect repair using bilayered hydrogels encapsulating both chondrogenically and osteogenically pre-differentiated mesenchymal stem cells in a rabbit model," Osteoarthritis Cartilage 22(9) (2014), pp. 1291-1300.
Lee, et al., "Regeneration of the articular surface of the rabbit synovial joint by cell homing: a proof of concept study," Lancet 376 (9739), (2010), pp. 440-448.
Li, et al., "The Effect of Oxygen Tension on Human Articular Chondrocyte Matrix Synthesis: Integration of Experimental and Computational Approaches," Biotechnol. Bioeng. 111(9), (2014), pp. 1876-1885.
Lin et al., "Allyl sulfides are privileged substrates in aqueous cross-metathesis: application to site-selective protein modification," Journal of the American Chemical Society, 130 (2008), pp. 9642-9643.
Long et al., "Improving the mechanical properties of collagen-based membranes using silk fibroin for corneal tissue engineering," Journal of Biomedical Materials Research Part A, 103 (2015), pp. 1159-1168.

Lotz, M.K., "Posttraumatic osteoarthritis: pathogenesis and pharmacological treatment options," Arthritis Res. Ther. 12(3) (2010).
Ma et al., "Enhanced biological stability of collagen porous scaffolds by using amino acids as novel cross-linking bridges," Biomaterials, 25 (2004), pp. 2997-3004.
Mak, et al., "Indian hedgehog signals independently of PTHrP to promote chondrocyte hypertrophy," Development 135(11) (2008), pp. 1947-1956.
Mariani, et al., "Signaling Pathways in Cartilage Repair," International Journal of Molecular Science 15(5): (2014), pp. 8667-8698.
Mercado, et al., "Effect of grafting BMP2-derived peptide to nanoparticles on osteogenic and vasculogenic expression of stromal cells," Journal of Tissue Eng. Regen. Med. 8(1): (2014), pp. 15-28.
Mi, et al., "Adverse effects of adenovirus-mediated gene transfer of human transforming growth factor beta 1 into rabbit knees," Arthritis Res. Ther. 5(3): (2003), pp. R132-R139.
Moeinzadeh et al., "B13Nanostructure Formation and Transition from Surface to Bulk Degradation in Polyethylene Glycol Gels Chain-Extended with Short Hydroxy Acid Segments," Biomacromolecules, 14 (2013), pp. 2917-2928.
Moeinzadeh et al., "Gelation Characteristics and Osteogenic Differentiation of Stromal Cells in Inert Hydrolytically Degradable Micellar Polyethylene Glycol Hydrogels," Biomacromolecules, 13 (2012), pp. 2073-2086.
Munoz-Pinto et al., "Collagen-mimetic hydrogels promote human endothelial cell adhesion, migration and phenotypic maturation," Journal of Materials Chemistry B. 3 (2015), pp. 7912-7919.
Namba, et al., "Spontaneous repair of superficial defects in articular cartilage in a fetal lamb model." J. Bone Joint Surg. Am. vol. 80A(1): (1998), pp. 4-10.
Nichol et al., "Cell-laden microengineered gelatin methacrylate hydrogels," Biomaterials, 31 (2010), pp. 5536-5544.
Orth, et al., "Reliability, Reproducibility, and Validation of Five Major Histological Scoring Systems for Experimental Articular Cartilage Repair in the Rabbit Model," Tissue Eng. Part C Methods 18(5): (2012), pp. 329-339.
Pace et al., "A Human Hair Keratin Hydrogel Scaffold Enhances Median Nerve Regeneration in Nonhuman Primates: An Electrophysiological and Histological Study," Tissue Engineering Part A, 20 (2014), pp. 507-517.
Pascher, et al., "Gene delivery to cartilage defects using coagulated bone marrow aspirate," Gene Ther. 11(2): (2004), pp. 133-141.
Patel et al., "Biodegradable polymer scaffold for tissue engineering," Trends in Biomaterials and Artificial Organs, 25 (2011), pp. 20-29.
Pfaff, K. "A third of soldiers disabled ACI for lesions in the knee," Orthopedics Today (2014).
Rivera, et al, "Posttraumatic osteoarthritis caused by battlefield injuries: the primary source of disability in warriors," Journal Am. Acad. Orthop. Surg. 20(1): (2012), pp. S64-S69.
Rivera, et al, "The burden of posttraumatic arthritis," AAOS/OTA/SOMOS/ORS Extremity War Injuries VIII: Sequelae of Combat (2013).
Rouse et al., "A Review of Keratin-Based Biomaterials for Biomedical Applications," Materials, 3 (2010), pp. 999-1014.
Saravanan et al., "Exploration on the Amino Acid Content and Morphological Structure in Chicken Feather Fiber," Journal of Textile and Apparel, Technology and Management, 7-3, (2012).
Sawada et al., "Scaffold for Cell Culture Made by Electrospun Keratin Nanofibers" (Abstract Only), Tissue Engineering Part A, 20 (2014), p. S65.
Simank, et al., "Effects of local application of growth and differentiation factor-5 (GDF-5) in a full-thickness cartilage defect model," Growth Factors 22(1): (2004), pp. 35-43.
Stenman et al., "Trypsin-2 degrades human type II collagen and is expressed and activated in mesenchymally transformed rheumatoid arthritis synovitis tissue," American Journal of Pathology, 167 (2005), pp. 1119-1124.
Stockwell, R.A. "Interrelationship of Cell Density and Cartilage Thickness in Mammalian Articular Cartilage," Journal of Anatomy 109: (1971), pp. 411-421.

(56) References Cited

OTHER PUBLICATIONS

Studer, et al., "Molecular and Biophysical Mechanisms Regulating Hypertrophic Differentiation in Chondrocytes and Mesenchymal Stem Cells," Eur. Cells Mater. 24: (2012), pp. 118-135.
Tan et al., "Fabrication and Evaluation of Porous Keratin/chitosan (KCS) Scaffolds for Effectively Accelerating Wound Healing," Biomedical and Environmental Sciences, 28 (2015), pp. 178-189.
Tanabe et al., "Fabrication and characterization of chemically crosslinked keratin films," Materials Science and Engineering: C, 24 (2004), pp. 441-446.
Tropel et al., "Isolation and characterization of mesenchymal stem cells from adult mouse bone marrow," Experimental Cell Research, 295 (2004), pp. 395-406.
Verma et al., "Preparation of scaffolds from human hair proteins for tissue-engineering applications," Biomedical materials, 3-2 (2008), 025007.
Verschure, et al., "Localization of insulin-like growth factor-1 receptor in human normal and osteoarthritic cartilage in relation to proteoglycan synthesis and content," Br. J. Rheumatol. 35(11): (1996), pp. 1044-1055.
Visser, et al., "Crosslinkable Hydrogels Derived from Cartilage, Meniscus, and Tendon Tissue" Tissue Eng. Part A 21(7-8): (2015), pp. 1195-1206.
Wagegg, et al., "Hypoxia Promotes Osteogenesis but Suppresses Adipogenesis of Human Mesenchymal Stromal Cells in a Hypoxia-Inducible Factor-1 Dependent Manner," PloS One 7(9): (2012), e46483 10.
Wang et al., "Human keratin hydrogels support fibroblast attachment and proliferation in vitro," Cell and Tissue Research, 347 (2012), pp. 795-802.
Wang, et al., "TGF β signaling in cartilage development and maintenance," Birth Defects Res. Part C Embryo Today Rev. 102(1): (2014), pp. 37-51.
Watson, et al., "Gene delivery of TGF-β 1 induces arthrofibrosis and chondrometaplasia of synovium in vivo," Laboratory Investigation, 90(11): (2010), pp. 1615-1627.
Wehling, et al., "Interleukin-1 β and Tumor Necrosis Factor α Inhibit Chondrogenesis by 16 Human Mesenchymal Stem Cells Through NF-κ B-Dependent Pathways," Arthritis Rheum. 60(3): (2009), pp. 801-812.
Williamson, et al., "Growth of immature articular cartilage in vitro: Correlated variation in tensile biomechanical and collagen network properties," Tissue Eng. 9(4): (2003), pp. 625-634.
Wong, et al., "Chondrocyte biosynthesis correlates with local tissue strain in statically compressed adult articular cartilage," Journal of Orthop. Res. 15(2): (1997), pp. 189-196.
Wu, et al. "Human developmental chondrogenesis as a basis for engineering chondrocytes from pluripotent stem cells," Stem Cell Reports 1(6): (2013), pp. 575-589.
Xu et al., "Water-Stable Three-Dimensional Ultrafine Fibrous Scaffolds from Keratin for Cartilage Tissue Engineering," Langmuir, 30 (2014), pp. 8461-8470.
Yamauchi et al., "Preparation of stable aqueous solution of keratins, and physiochemical and biodegradational properties of films," Journal of Biomedical Materials Research, 31 (1996), pp. 439-444.
Yang, et al., "Engineering Orthopedic Tissue Interfaces," Tissue Engineering Part B Rev. 15(2): (2009), pp. 127-141.
Yin et al., "Study on effective extraction of chicken feather keratins and their films for controlling drug release," Biomaterials Science, 1 (2013), pp. 528-536.
Yue et al., "Synthesis, properties, and biomedical applications of gelatin methacryloyl (GelMA) hydrogels," Biomaterials, 73 (2015), pp. 254-271.
Zhang, et al., "The role of tissue engineering in articular cartilage repair and regeneration," Crit. Rev. Biomed. Eng. 37(1-2): (2009), pp. 1-57.
Jayasuriya, et al. "The influence of tissue microenvironment on stem cell-based cartilage repair" *Ann. NY Acad. Sci.* 1383 (2016) pp. 21-33.
Lin, et al. "PEG hydrogels for the controlled release of biomolecules in regenerative medicine" *Pharm. Res.* 26 (2009) pp. 631-643.
Wang, et al. "Culturing fibroblasts in 3D human hair keratin hydrogels" *Appl. Mater. Interf.* 7 (2015) pp. 5187-5198.

\* cited by examiner

COMPOSITIONS AND LAYERED STRUCTURES FORMED THEREWITH FOR REGENERATION OF ARTICULAR CARTILAGE

CROSS REFERENCE TO RELATED APPLICATION

This application claims filing benefit of U.S. Provisional Patent Application Ser. No. 62/468,539 having a filing date of Mar. 8, 2017, entitled "Composition for in situ Zonal Regeneration of Articular Cartilage," which is incorporated herein by reference for all purposes.

BACKGROUND

Articular cartilage is structurally and functionally composed of multiple distinct zones including superficial, middle and calcified zones with each zone exhibiting a defined function and extra cellular matrix (ECM) composition. The superficial zone is characterized by pre-chondrocytes with high expression of superficial zone protein (SZP) for joint lubrication. The middle zone is characterized by pre-hypertrophic chondrocytes with high expression of glycosaminoglycans (GAG) and aggrecans (AGCs) for compressive strength. The calcified zone is characterized by hypertrophic chondrocytes with high expression of collagen type X (Col X) and alkaline phosphatase (ALP) for the formation of a mineralized matrix.

During embryonic development of cartilage, mesenchymal stem cells (MSCs) condense by up-regulation of transforming growth factor-β1 (TGFβ1) signaling. The condensed MSCs differentiate into pre-chondrocytes by co-expression of TGFβ1 and bone morphogenetic protein-7 (BMP7) to form a matrix remarkably similar to the superficial zone of articular cartilage. Next, the developing fetal cartilage divides into two morphologically distinct zones, namely the superficial and middle zones, by further differentiation of pre-chondrocytes to pre-hypertrophic chondrocytes driven by the gradients in BMP7 and insulin-like growth factor-1 (IGF1). In a similar process, the cells further away from the synovial cavity mature into hypertrophic chondrocytes by gradients in BMP7, IGF1, and Indian Hedgehog (IHH) to generate the complete zonal organization (superficial, middle, calcified) of articular cartilage. Early morphogenetic events are also significantly affected by the local environment of the developing tissue. For instance, during the embryonic development of cartilage, in addition to the sequential expression of morphogens, the extracellular matrix (ECM) motifs in fetal articular cartilage play a significant development role.

Unfortunately, while fetal articular cartilage injuries are able to heal spontaneously and avoid fibrous scar tissue, postnatal articular cartilage lacks the ability for complete self-repair. A significant consequence of traumatic extremity injuries and the inability for self-repair of articular cartilage is post-traumatic osteoarthritis (PTOA). The rapidly applied load in traumatic injuries focally disrupts the articular cartilage beginning with cell death, decreased stiffness and rapid progression to a full-thickness defect with time. Approximately 12% of all osteoarthritis (OA) cases are caused by post-traumatic osteoarthritis (PTOA). About 3.5 million individuals in US suffer from PTOA of the hip, knee, or ankle with a total cost of $3 billion to the health care system. PTOA can occur in any age from any acute physical trauma such as sport, vehicle accident, fall, or military injury.

Conventional clinical approaches to treatment of full-thickness chondral defects such as subchondral drilling, microfracture, and abrasion arthroplasty create mechanically-inferior fibrocartilage. Osteochondral autograft transfer or mosaicplasty suffers from an additional surgical intervention and donor site morbidity. Autologous chondrocyte implantation (ACI) fails to restore zonal organization of the articular cartilage and in some cases leads to peripheral hypertrophy and calcification. For example, 33% of ACI procedures performed on soldiers suffering from PTOA of the knee resulted in permanent disability. Tissue engineered (TE) articular cartilage grafts have also been developed. As the middle zone is the thickest layer and bears the bulk of the compressive load, most TE articular cartilage grafts are based on mimicking the properties of the middle zone. However, these grafts have been shown to degenerate into biologically inferior fibrocartilage tissue.

What are needed in the art are improved compositions for use in reconstruction and repair of articular cartilage that can more closely mimic and encourage the body's natural tissue formation mechanisms. For instance, injectable therapies and implantable graft materials that can regenerate the zonal microstructure of articular cartilage would be of great benefit in the art, and have the potential to prevent permanent disability in patients suffering from PTOA.

SUMMARY

A composition is disclosed for use in regeneration of articular cartilage. The composition includes nano-sized particles (i.e., nanogels) that include a crosslinked polymer conjugated to a signaling molecule (e.g., a protein or a functional fragment of a protein) that stimulates articular cartilage formation or repair. For example, a signaling molecule can include an expression product that has efficacy in stem cell differentiation and articular cartilage formation (e.g., TGFβ1, BMP7, IGF1, IHH, etc.). The crosslinked polymer of the nanogel is designed to degrade over a predetermined time period and thus provide for sustained release of the signaling molecule.

The composition can also include a plurality of microcapsules; each of which can carry a plurality of the nanogels. The microcapsules include a bioerodable polymer that is designed to exhibit a controlled release profile for the nanogels carried inside. As such, the release of the nanogels (and the subsequent sustained release of the signaling molecule carried by the nanogels) can be controlled and optionally delayed from the composition.

The composition can also include a crosslinkable polymer. Following placement/formation of the composition, the polymer can be crosslinked by application of energy (e.g., UV crosslinking, temperature-based crosslinking, etc.) so as to form a semi-solid, crosslinked hydrogel.

The crosslinkable composition can include a plurality of the microcapsules (that each carry a plurality of nanogels) as well as additional components useful in articular cartilage formation or repair. For instance, a composition can carry differentiated or stem cells (e.g., mesenchymal stem cells) that can be affected by the sequential release of the signaling molecules from the nanogels. The composition can also carry ECM components of articular cartilage. For instance, a composition can include a fetal articular cartilage ECM mimetic.

According to another embodiment, disclosed is a multi-layered articular cartilage implant. For instance, the multi-layer implant can include a first hydrogel layer that includes microcapsule/nanogel composites in which a polymer of the nanogels is conjugated with a signaling molecule that stimulates formation or repair of the superficial zone of articular cartilage (e.g., BMP-7). The multilayer implant can include a second hydrogel layer that includes microcapsule/nanogel composites in which a polymer of the nanogels is conjugated with a signaling molecule that stimulates formation or repair of the middle zone of articular cartilage (e.g., IGF1). The multilayer implant can also include a third hydrogel layer that includes microcapsule/nanogel composites in which a polymer of the nanogels is conjugated with a signaling molecule that stimulates formation or repair of the calcified zone of articular cartilage (e.g., IHH). One or more layers of the implant can also include nanogels in which a polymer of the nanogels is conjugated to TGFβ1. The TGFβ1 can be conjugated in nanogels that also carry a second signaling molecule, TGFβ1-conjugated nanogels can be combined with other nanogels that carry a second signaling molecule in the same microcapsules, or TGFβ1-conjugated nanogels can be incorporated in microcapsules that only carry the TGFβ1-conjugated nanogels. In any case, the microcapsules of a layer can thereby release both TGFβ1 and a second signaling molecule (e.g., BMP7, IGF1, or IHH) according to a predesigned release profile to stimulate formation/repair of articular cartilage. One or more of the layers of the implant can also carry differentiated or stem cells (e.g., mesenchymal stem cells) and/or ECM components of articular cartilage.

A method for forming a multi-layered articular cartilage implant is also disclosed. For instance, a method can include forming a first composition that includes microcapsule/nanogel composites in which a polymer of the nanogels is conjugated with a signaling molecule that stimulates formation or repair of the superficial zone of articular cartilage (e.g., BMP-7). This composition can then be partially crosslinked to form a first layer. Following, a second composition that includes microcapsule/nanogel composites in which a polymer of the nanogels is conjugated with a signaling molecule that stimulates formation or repair of the middle zone of articular cartilage (e.g., IGF1) can be located on the first layer, and this second layer can then be partially crosslinked. Following, a third composition that includes microcapsule/nanogel composites in which a polymer of the nanogels is conjugated with a signaling molecule that stimulates formation or repair of the calcified zone of articular cartilage (e.g., IHH) can be located on the second layer, and this third layer can then be crosslinked. One or more of the compositions can also incorporate nanogels in which a polymer of the nanogel is conjugated to TGFβ1. One or more of the compositions can also include differentiated or stem cells (e.g., mesenchymal stem cells) and/or extracellular matrix components of articular cartilage.

BRIEF DESCRIPTION OF THE FIGURES

A full and enabling disclosure of the present subject matter, including the best mode thereof to one of ordinary skill in the art, is set forth more particularly in the remainder of the specification, including reference to the accompanying figures in which.

Repeat use of reference characters in the present specification and drawings is intended to represent the same or analogous features or elements of the present invention.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed herein are compositions and products incorporating the compositions for use in repair or generation of articular cartilage. In one particular embodiment, the compositions can be utilized to form a multi-layer implant that can more closely mimic the multi-zonal structure of natural cartilage. The compositions are hydrogel-based compositions that can be crosslinked following formation and that are designed to sequentially release signaling molecules that encourage formation or repair of articular cartilage. The compositions can also carry additional components to encourage articular cartilage repair or formation. For instance, a composition can carry cells (either differentiated cells or stem cells) that can interact with the signaling molecules in cartilage repair/generation. In addition, a composition can carry extracellular matrix (ECM) components that can further encourage cartilage generation.

The compositions and hydrogel layers formed of the compositions described herein allow for not only the sustained release of signaling molecules (e.g., proteins or functional fragments thereof) to stimulate articular cartilage healing/generation, but also allow for the delayed release of signaling molecules and provide zonal organization of signaling molecules, in order that the sequential signaling and concentration gradients naturally present in articular cartilage formation can be mimicked in tissue engineering applications. In the absence of sequential and sustained delivery, signaling molecules that are merely located at a desired site of activity will diffuse away from the site of regeneration within a few hours and concentration gradients necessary for desired biological activity will not be present.

In formation of the compositions, signaling molecules such as articular cartilage morphogens can be conjugated to polymers in the form of nanogels so as to provide for sustained release of the signaling molecules from the encapsulating nanogels. In addition, the nanogels that carry the signaling molecules can be encapsulated in microcapsules that can provide for delayed release of the nanogels. Through combination of the nanogels and the microcapsules, optionally in conjunction with additional tissue engineering components (e.g., ECM components, stem cells, etc.), the compositions can more closely mimic natural articular cartilage generation mechanisms.

Figure 1:
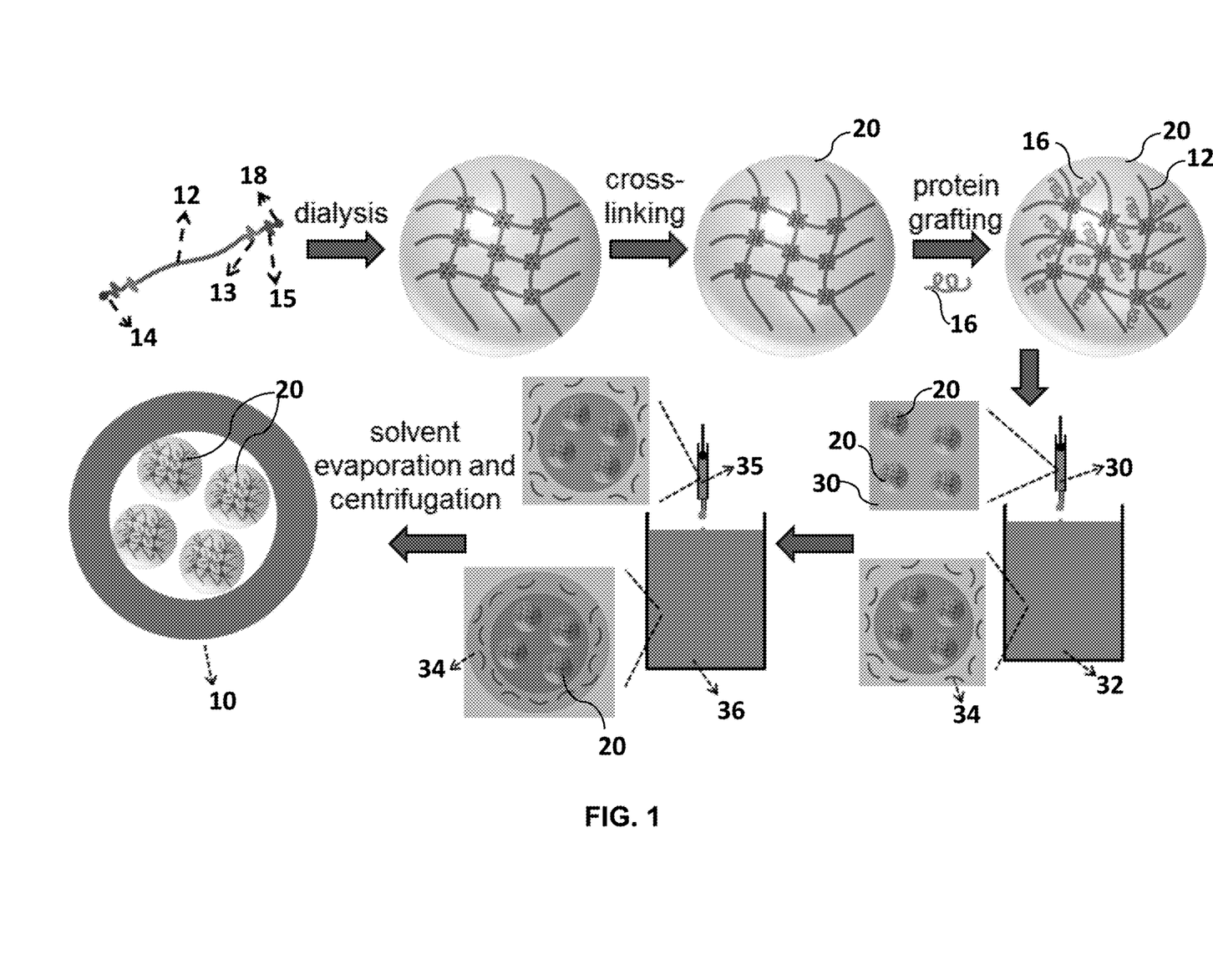
FIG. 1 schematically illustrates a synthesis process as may be utilized in formation of a composition as described herein.

FIG. 1 schematically illustrates one embodiment for formation of the composite microcapsule/nanogel structures of a composition. As shown, a composite structure can include a microcapsule 10 that encapsulates a plurality of nanogels 20. Each nanogel 20 includes a polymer 12 that in turn includes a first functionality 14 configured for conjugation with a signaling molecule 16 and a second functionality 18 configured for crosslinking of the polymer. The combination of microcapsules 10 that can be designed to delay release of the contents with the sustained releasing nanogels 20 held within the microcapsules can provide for delayed/sustained-release of the signaling molecules 16.

The nanogels 20 can be formed of a biocompatible polymer 12 that can be derivatized as necessary so as to be crosslinkable via the presence of a functionality 18, controllably degradable in a biological environment (e.g., hydrolysable), and capable of conjugation to signaling molecules 16 via the presence of a reactive functionality 14.

Any hydrophilic polymer can be used as a base for the synthesis of nanogels. In one embodiment, the nanogels can be based upon a polyethylene glycol (PEG) polymer. Other hydrophilic polymers that can be used can include, without limitation, polyvinyl alcohol, polyvinyl pyrrolidinone, polyacrylic acid, poly(2-hydroxyethylmethacrylate), poly(acrylamide), and the like as well as mixtures of the aforementioned hydrophilic polymers. PEG-based hydrogels are inert, non-immunogenic, compatible with biological components (e.g., stem cells) and can be derivatized relatively easily. Due to their inert nature, PEG hydrogels provide enormous flexibility in design and control of the local microenvironment. The inert nature of PEG can also minimize adsorption and denaturation of signaling molecules (e.g., proteins) incorporated in the nanogels, which could otherwise adversely affect the composition function, and can stabilize the signaling molecules by reducing aggregation. Beneficially, flexible PEG polymers can crosslink to produce hydrogels with high compressive modulus without adversely affecting the function of the conjugated signaling molecules. The PEG polymers can impart stability to the nanogels in aqueous solution.

In general, the polymer 12 used in formation of the nanogels 20 can have a number average molecular weight of from about 4 kDa to about 12 kDa.

In order to control self-assembly of the polymers 12 in the initial formation of the nanogels and to control degradation of the nanogels according to a desired sustained release profile for the conjugated signaling molecules, the polymer 12 can be chain extended at the termini with relatively short hydrophobic segments 13, 15 that include a series of hydrophobic monomers. For instance, a hydrophobic segment can include from about 4 to about 20 hydrophobic monomers, which can be the same or different as one another. The hydrophobic monomers can include any biocompatible hydrophobic monomers such as, without limitation, lipid monomers, anyhydride monomers, orthoester monomers, phosphazene monomers, hydroxy acid monomers, and the like as well as mixtures of hydrophobic monomers. For instance, the hydrophobic segment can include, without limitation, glycolide monomers, lactide monomers, dioxanone monomers, ε-caprolactone monomers, hydroxy butyrate monomers, valcrolactone monomers, malonic acid monomers, as well as mixtures of monomers.

In one embodiment, a hydrophobic segment of a polymer 12 terminus can include a first length 13 that includes a series of lactide monomers that can regulate self-assembly of the nanogels and a second length 15 that includes a series of glycolide monomers that can aid in control of the degradation rate of the nanogel. Each length 13, 15 of a hydrophobic segment can be about 10 monomer units in length or less. For instance, the length 13 of lactide monomers can generally include from 2 to about 9 monomer units and the length 15 of glycolide monomers can generally include from 1 to about 6 monomer units.

The short hydrophobic segments 13, 15 can be bonded to the polymer 12 according to any suitable process, such as by combining the polymer with the hydrophobic monomer under reactive conditions with a catalyst, e.g., a tin(II)2-ethylhexanoate catalyst.

Without wishing to be bound to any particular theory, it is believed that the short hydrophobic segments can be sequestered within the core of the nanogels formed during the crosslinking reactions. In addition, the crosslinking moieties and any initiators used in conjunction with the crosslinking reaction can be sequestered within the nanogel core. By sequestering self-assembly, gelation and degradation components within the crosslinked nanogel structures, potential cytotoxicity of the nanogels to cells or other components of the composition can be reduced.

Furthermore, the size of each individual nanogel can be controlled by components used to form the nanogel particles (e.g., the polymer size and relative hydrophobicity of the short terminal segments), and the nanogel size can affect the degradation rate of the nanogels. The degradation rate of the nanogels and sustained release of the signaling molecules carried in the nanogels can be tuned from a few days to many months through variation of the polymer size as well as the characteristics of the hydrophobic end segments. The hydrolysis rate of the nanogels can be strongly dependent on the number and type of hydrophobic monomers in the hydrophobic segment. For instance, a nanogel that incorporates a less hydrophobic monomer, such as glycolide, can release the signaling molecules over the course of a few days while one that incorporates a more hydrophobic monomer, such as ε-caprolactone, can release the signaling molecules over the course of many months.

The polymers 12 can also be functionalized with a reactive functionality 18 that can provide for crosslinking of the polymers 12 and formation of stable nanogels 20. Accordingly, in addition to the chain extension of the polymers with the hydrophobic segments, a polymer 12 can be further processed to promote crosslinking of the polymer and formation of the crosslinked nanogels. For example, to crosslink the polymers 12 via UV, the polymer 12 can be functionalized at the termini to have UV-crosslinkable functionality 18. Such groups are typically acrylates or methacrylates. The general scheme can include replacing terminal hydroxyl and/or carboxylic acid groups of a hydrophobic segment with acrylate or methacrylate functionality according to standard practice.

Crosslinking may be carried out via self-crosslinking of the polymer and/or through the inclusion of a separate crosslinking agents and/or initiators. Suitable crosslinking agents, for instance, may include polyglycidyl ethers, such as ethylene glycol diglycidyl ether and polyethylene glycol dicglycidyl ether; acrylamides; compounds containing one or more hydrolyzable groups, such as alkoxy groups (e.g., methoxy, ethoxy and propoxy); alkoxyalkoxy groups (e.g., methoxyethoxy, ethoxyethoxy and methoxypropoxy); acyloxy groups (e.g., acetoxy and octanoyloxy); ketoxime groups (e.g., dimethylketoxime, methylketoxime and methylethylketoxime); alkenyloxy groups (e.g., vinyloxy, isopropenyloxy, and 1-ethyl-2-methylvinyloxy); amino groups (e.g., dimethylamino, diethylamino and butylamino); am inoxy groups (e.g., dimethylaminoxy and diethylaminoxy); and amide groups (e.g., N-methylacetamide and N-ethylacetamide).

If included, an initiator can be used to initiate crosslinking of the polymer 12. Examples of UV initiators include, without limitation, IRGACURE® 184 (1-hydroxycyclohexyl phenyl ketone), and DAROCURE® 1173 (α-hydroxy-1, α-dimethylacetophenone) which are both commercially available from Ciba-Geigy Corp. Additional examples of initiators (which may be UV-initiators, thermal initiators, or other types of initiators) may include, without limitation, benzoyl peroxide, azo-bis-isobutyro-nitrile, di-t-butyl peroxide, bromyl peroxide, cumyl peroxide, lauroyl peroxide, isopropyl percarbonate, methylethyl ketone peroxide, cyclohexane peroxide, t-butylhydroperoxide, di-t-amyl peroxide, dicymyl peroxide, t-butyl perbenzoate, benzoin alkyl ethers (such as benzoin, benzoin isopropyl ether, and benzoin isobutyl ether), benzophenones (such as benzophenone and methyl-o-benzoyl benzoate), acetophenones (such as acetophenone, trichloroacetophenone, 2,2-diethoxyacetophenone, p-t-butyltrichloro-acetophenone, 2,2-dimethoxy-2-phenylacetophenone, and p-dimethylaminoacetophenone), thioxanthones (such as xanthone, thioxanthone, 2-chlorothioxanthone, and 2-isopropyl thioxanthone), benzyl 2-ethyl anthraquinone, methylbenzoyl formate, 2-hydroxy-2-methyl-1-phenyl propane-1-one, 2-hydroxy-4'-isopropyl-2-methyl propiophenone, e-hydroxy ketone, tet-remethyl thiuram monosulfide, allyl diazonium salt, and a combination of camphorquinone or 4-(N,N-dimethylamino) benzoate.

Any of a variety of different crosslinking mechanisms may be employed, such as thermal initiation (e.g., condensation reactions, addition reactions, etc.), electromagnetic radiation, and so forth. Some suitable examples of electromagnetic radiation that may be used include, but are not limited to, electron beam radiation, natural and artificial radio isotopes (e.g., α, β, and γ rays), x-rays, neutron beams, positively-charged beams, laser beams, ultraviolet, etc. The wavelength λ of the radiation may vary for different types of radiation of the electromagnetic radiation spectrum, such as from about $10^{-14}$ meters to about $10^{-5}$ meters. Besides selecting the particular wavelength λ of the electromagnetic radiation, other parameters may also be selected to control the degree of crosslinking. For example, the dosage may range from about 0.1 megarads (Mrads) to about 10 Mrads, and in some embodiments, from about 1 Mrads to about 5 Mrads.

In one embodiment, the polymer 12 can be acrylate-functionalized 18 at one chain-end. For instance, a PEG polymer that has been previously functionalized with short lactide/glycolide segments at the termini can be reacted with acryloyl chloride in 1:1 molar ratio to produce a functionalized polymer that includes an acrylate at one chain-end.

In addition to short hydrophobic control segments 13, 15 and crosslinkable functionality 18, the polymer 12 can also be functionalized so as to enable conjugation with the desired signaling molecule 16. For instance, a polymer 12 can be end-functionalized with succinimide by reaction with N,N'-disuccinimidyl carbonate according to standard practice.

In general, the functionalized polymers 12 will be crosslinked prior to conjugation with the desired signaling molecules. For instance, the functionalized polymers can be assembled in aqueous solution by dialysis and crosslinked (e.g., via UV radiation) to generate water-swollen nanogels 20. Following functionalization and crosslinking, the nanogels 20 can generally have a largest dimension of from about 10 nanometer to about 100 nanometers.

The signaling molecule 16 of choice can be conjugated to the crosslinked nanogels by reaction between the nanogel functionality 18 (e.g., a succinimide group) and a functionality of the signaling molecule (e.g., an amine group). By conjugation in the nanogels 20, the signaling molecule 16 can be prevented from diffusion into the organic phase of the encapsulating microcapsules and can be sequestered from release until the degradation of the surrounding microcapsule, upon which the nanogels can release the conjugated signaling molecule 16 according to the engineered sustained release profile.

A nanogel 20 may include as a signaling molecule 16 any biologically active compound (or combination thereof) as may affect the healing or generation of articular cartilage. For instance, a nanogel 20 can include a signaling molecule 16 that can act as a signal for modifying cell adhesion, growth, or migration, for instance in stimulating or promoting the adhesion, growth, or migration of the desirable cells, and/or inhibiting or stimulating the adhesion, growth, or migration of undesirable cells. Such compounds can include growth factors, hormones, extracellular matrix proteins and other cellular adhesion peptides identified in the extracellular matrix protein. Suitable signaling molecules may include, for example, TGFβ1, BMP7, IGF1, IHH, or other signaling molecules involved in the generation or repair of cartilage. Examples of extracellular matrix proteins include fibronectin, collagens, laminins, and vitronectins, and the tri-peptide RGD (arginine-glycine-aspartate) that is found in many of the extracellular matrix proteins. Signaling molecules that inhibit or stimulate undesired cells, such as cancerous cells or inflammatory cells can be included.

A signaling molecule may also include a small molecule such as a bisphosphonate that can prevent the loss of bone mass. Another example of a small molecule signaling molecule is an antibiotic that can prevent bacterial contamination. Examples of small molecule bisphosphonates include, without limitation, Etidronate, Clodronate, Tiludronate, Pamidronate, Neridronate, Olpadronate, Alendronate, Ibandronate, Risedronate, Zoledronate, and the like as well as mixtures of bisphosphonates. Example of antibacterial agents include, without limitation, gentamicin, tetracycline, vancomycin, ibuprofen, dexamethasone, ciprofloxacin, gatifloxacin, polymyxin B and the like as well as mixtures of the antibacterial small molecules. Of course, different types of signaling molecules (e.g., proteinaceous and small molecule, bisphosphonates and antibacterial agents, etc.) can be combined in individual nanogels or in different nanogels held in the same or different microcapsules of a composition.

In general, the nanogels 20 can include the signaling molecules 16, which can be the same or different from one another in a single nanogel, in a concentration of from about 0.5 µg/mL to about 4 µg/mL per 20 mg of nanogels.

In forming a composition, a plurality of signaling molecule-conjugated nanogels 20 can be encapsulated in a polymer microcapsule 10 that can provide for delayed release of the nanogels 20 and the signaling molecules 16 carried by the nanogels 20. For instance, and as schematically illustrated in FIG. 1, a plurality of nanogels 20 can be encapsulated in a polylactide-based polymer microcapsule 10 according to a water-oil-water (w-o-w) double emulsion technique for delayed release of the signaling molecules. The polymer utilized in formation of the microcapsule 10 can be selected to provide a desired degradation rate and delay. For instance, a poly(lactide-co-glycolide) (PLGA)-based microcapsule can be selected in design of materials for relatively rapid release of the contained nanogels (e.g., delays of up to about 6 weeks), while more hydrophobic polymers such as poly(lactide-co-caprolactone) (PLCL) copolymer may be preferred to achieve longer delay times and release rates from the microcapsules. Polylactide homopolymer as well as other lactide-based copolymers as are known in the art may alternatively be utilized in formation of the microcapsules. In general, any hydrophobic polymer that can form microcapsules in aqueous solution can be used. Examples include, without limitation polyanhydrides, polyorthoesters, polyphosphazenes, polypropylene fumarate, polyhydroxyacids, polyhydroxybutyrate, polyvalcrolactone, polymalonic acid as well as mixtures of polymers.

A double emulsion w-o-w encapsulation technique as may be utilized in forming the microcapsules 10 and as schematically illustrated in FIG. 1 can generally include dispersing the nanogels 20 in a first aqueous phase 30. Following, the aqueous phase 30 can be dispersed in a suitable organic phase 32 comprising an organic solution of the polymer (e.g., a poly(D,L lactide-co-glycolide) polymer) 34, the organic phase 32 being non-miscible with the aqueous phase 30. For example, a nanogel dispersion including about 0.1 mg nanogels/mL or greater, or from about 1 mg/mL to about 100 mg/mL or even greater in some embodiments can be injected (such as with a 25 gauge needle) into the organic polymer phase 32 while homogenizing, e.g., at about 15,000 to 25,000 rpm.

By way of example, an aqueous phase 30 including the nanogels 20 can be initially emulsified in an organic phase 32 including PLGA polymer of a predetermined molecular weight, poly(lactide-co-ethylene oxide fumarate) (PLEOF) as emulsifying agent, and chloroform as organic solvent. Other organic solvents and emulsifying agents as are known in the art may alternatively be utilized. For instance, organic solvents can include, without limitation, methylene chloride, ethyl acetate with or without benzyl alcohol or acetone, and combinations of organic solvents.

After this first homogenization (generally about 0.5 to about 5 minutes, for instance for about 1 minute), this emulsion 35 is added to a second aqueous emulsification solution 36 to form a second emulsion. The second emulsification aqueous solution 36, can be for instance a polyvinyl alcohol solution, optionally including ethyl acetate. The w-o-w emulsion mixture is mixed at high speed (generally about 1700 to 2500 rpm) to generate the microcapsules 10 including the polymer 34 surrounding the nanogels 20.

The stable microcapsules 10, each encapsulating a plurality of nanogels 20 can be formed and collected upon evaporation of the organic solvent (e.g., at ambient conditions, dependent upon the solvent) and centrifugation to remove the aqueous phase, as shown.

In one embodiment, microcapsules 20 can be formed with a largest external dimension of from about 1 µm to about 10 µm. However, the microcapsules are not limited to this size and larger materials may be preferred in certain applications. For example, when considering in vitro applications, it may be preferred to form larger microcapsules.

Design factors that may be modified to provide microcapsules with a desired size and degradation delay can include molecular weight and the type of polymer 34, emulsifier concentration in the organic phase, copolymer component ratio on a polymer (e.g., L:G ratio for a PLGA copolymer), and polymer concentration in the organic phase (affects capsule wall thickness). In general, lactide-based polymers (PLGA, PLCL, PLA, etc.) for use in the disclosed microcapsules can have a number average molecular weight of from about 5 kDa to about 75 kDa and a lactide copolymer ratio (e.g., L:G or L:C ratio) of from about 100:0 to about 50:50. The organic phase can generally include the emulsifying agent (e.g., the PLOEF) at a concentration of from about 5 wt. % to about 50 wt. %, and can include the lactide-based polymer at a concentration of from about 5 wt. % to about 15 wt. % in the organic solvent.

The composite nanogel/microcapsule can have a conjugation efficiency of the signaling molecules of greater than about 90% and a release level of greater than about 75%.

One or more types of nanogel/microcapsule composites can be incorporated in a hydrogel precursor composition for use in treatment or generation of articular cartilage. While a composition can include only one type of nanogel/microcapsule composites each loaded with only a single signaling molecule directed to a specific zone, this is not a requirement of the disclosed compositions. In some embodiments, a composition can include multiple different signaling molecules, either in the same nanogels and/or the same microcapsules as one another or in different nanogel/microcapsule composites. For instance, in one embodiment a composition can include both a zone-specific signaling molecule and a global signaling molecule. In one particular embodiment, a composition can include TGFβ1 as it is considered the master regulator of chondrogenesis in conjunction with a zone-specific morphogen, e.g., BMP-7, IGF1, or IHH).

Figure 2:
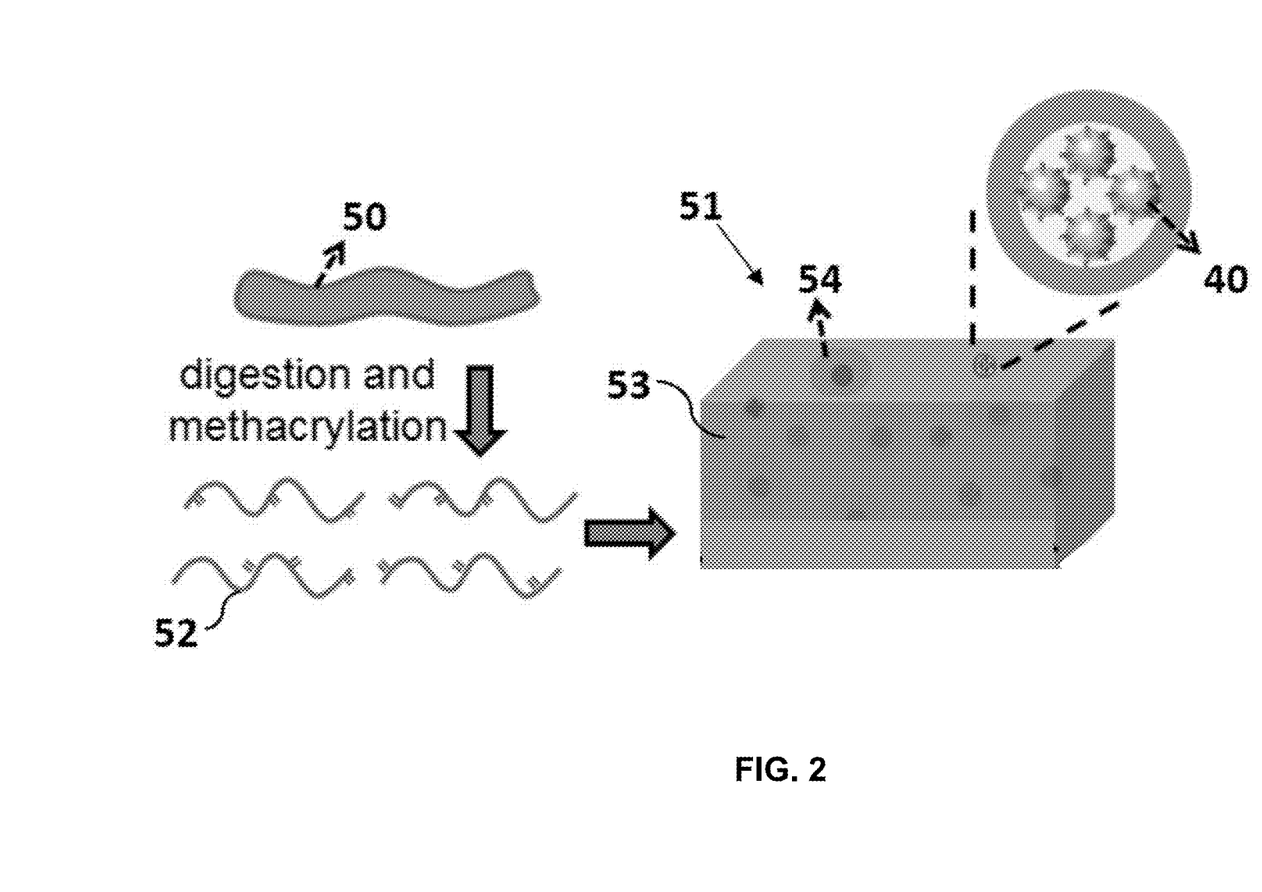
FIG. 2 schematically illustrates a composition synthesis process.

As illustrated in FIG. 2, a composition 51 can include nanogel/microcapsule composites 40 and a crosslinkable matrix-forming polymer 52. The matrix-forming polymer 52 can be crosslinked following formation or placement (e.g., injection) of the composition 51 to provide a hydrogel including a crosslinked matrix 53. In one embodiment, the crosslinkable polymer 52 can be based upon a natural biopolymer that can provide biocompatibility to the composition. In addition, the composition 51 can incorporate one or more additional components conducive to the desired tissue formation, e.g., ECM components. For example, and as illustrated in FIG. 2, a composition 51 can be derived from a natural tissue 50 (e.g., allograft or xenograft tissue) that can be decellularized, digested, and functionalized to provide the crosslinkable polymer 52 in conjunction with other components of the natural tissue 50 in an injectable, crosslinkable composition 51. As such, the composition 51 can provide both a crosslinkable polymer 52 capable of forming the hydrogel matrix 53 and natural components conducive to the tissue engineering application.

In one particular embodiment, the composition 51 can be based upon natural articular cartilage. As fetal articular cartilage is capable of spontaneous healing while avoiding fibrocartilage formation, in one particular embodiment, a crosslinkable polymer 52 can be derived from fetal articular cartilage, e.g., the composition 51 can be formed from fetal bovine articular cartilage that has been digested, decellularized and functionalized. A composition can be modified as necessary to provide a desired viscosity for pre-crosslinking processing as well as post-crosslinking characteristics. For instance, it may be desired to have a suitably high pre-crosslinking viscosity so as to maintain the hydrogel precursor composition at a location and/or having a particular form prior to crosslinking. In such an embodiment, a functional segment can be incorporated on the polymer. For instance, a temperature-sensitive N-isopropylacrylamide (NIPAM) segment, soluble below 25° C. but forming a gel at physiological temperature, can be grafted to the digested cartilage, e.g., by RAFT polymerization as described previously. A dual-mechanism gelation as may be provided by a second segment on the polymer can allow for immediate physical gelation for immobilization followed by UV crosslinking to reach the desired compressive modulus of the hydrogel product.

By way of example, fetal bovine cartilage can be decellularized by treatment with 10 mM Tris/1% triton, 1 U/mL deoxyribonuclease, and 1 U/mL ribonuclease. After freeze-drying, the decellularized material can be digested with pepsin until a clear suspension is obtained. The digested and decellularized material can then be functionalized to include a crosslinkable functionality (e.g., acrylate or methacrylate functionality) on the digested polymers. For instance, the material can be reacted with methacrylic anhydride to produce a methacrylated biopolymer-based crosslinkable polymer 52. Maximum added reactivity content of the biopolymer (e.g., acrylate functionality) can be such that will not significantly affect biocompatibility of the composition 51.

In one embodiment, a composition 51 (including all additives) can have a viscosity of from about 5 mPa-s to about 15 mPa-s, for instance so as to be injectable through a 0.43 mm microcatheter. However, as discussed above, in other embodiments a higher viscosity solution may be preferred, so as to form and crosslink the composition with a desired shape. A crosslinkable composition 51 can have a gelation time of about 1 min or less, and can have a compressive modulus following crosslinking of about 50 kPa to about 150 kPa, so as to support the developing tissue. However, viscosity, injectability, gelation time, and mechanical characteristics (e.g., compressive modulus) of the composition 51 and the crosslinked hydrogel 53 formed from the composition 51 are not limited to these values and can be varied, for instance depending upon the specific application of the composition.

Optionally, a composition 51 can also include cells 54 that can be affected by the release of the signaling molecules. Cells 54 contained in a composition 51 can include differentiated cells (e.g., chondrocytes) and/or stem cells. For instance, in one particular embodiment, a composition 51 can include mesenchymal stem cells (MSC).

Cells 54 can be loaded into a composition 51 at a density similar to that of the cartilage of interest or of a particular zone of the cartilage of interest. For instance, in one embodiment a composition 51 can incorporate mesenchymal stem cells at a density of from about 50 million cells/mL to about 200 million cells/m L, which corresponds to that of adult and fetal articular cartilage, respectively.

A composition including a limited number of signaling molecules directed to a particular zone of articular cartilage can be used as is, for instance through injection of the composition into a site of damaged cartilage.

In one embodiment, a plurality of compositions that vary with regard to one or more aspects, e.g., signaling molecules contained therein, cell loading presence or concentration, cell types, viscosity, etc., can form a multi-layer articular cartilage structure as may be utilized in one embodiment as an implant. For instance, a multi-layer structure can include a plurality of layers in which the nanogel/microcapsule composites of each layer can differ by release profile and signaling molecule. Thus, the implant can provide for delayed/sustained and sequential release of the signaling molecules (e.g., TGFβ1, BMP7, IGF1, and IHH) so as to stimulate repair or generation of articular cartilage.

Figure 3:
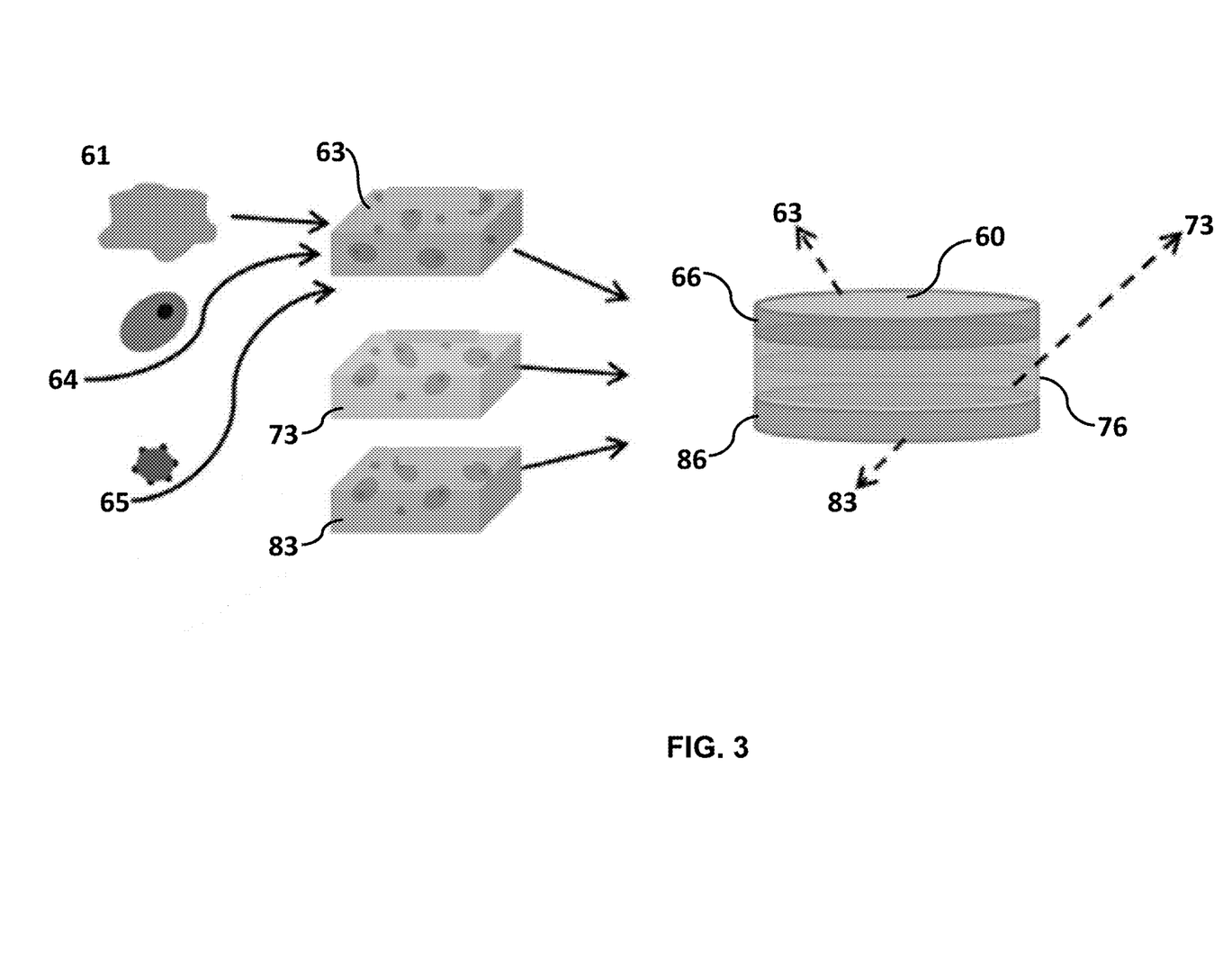
FIG. 3 schematically illustrates a synthesis process for a multi-layer articular cartilage implant as described herein.

One embodiment of a multi-layer structure 60 is schematically illustrated in FIG. 3. As shown, a multi-layer structure 60 can include a first crosslinked layer 63, a second crosslinked layer 73, and a third crosslinked layer 83. Each of the layers can be formed from a biocompatible composition that includes a crosslinkable polymer and optionally additional useful components, e.g., ECM components, etc. as discussed previously and can be loaded with nanogel/microcapsule composites and optionally also with cells that can be affected by release of the signaling agents from the nanogel/microcapsule composites. For example, as shown for the first layer 63, the layer can include a biocompatible crosslinkable composition 61, cells 64, and nanogel/microcapsule composites 65. The various components of each layer can be the same or different from one another. For instance, in one embodiment, every layer of a multi-layer structure 60 can include TGFβ-1-conjugated nanogel/microcapsule composites in conjunction with nanogel/microcapsule composites conjugated with a zone specific signaling molecule.

To form an implantable articular cartilage graft, a multi-layer structure 60 representing the zonal structure of articular cartilage can be generated layer by layer.

The following description provides one embodiment of a step-by-step formation approach as may be followed:

Step 1) A photo-crosslinkable fetal-based biopolymer derived from bovine fetal articular cartilage having the desired level of functionalization is mixed with a photoinitiator such as 4-(2-hydroxyethoxy)phenyl-(2-hydroxy-2-propyl) ketone (commercial name Irgacure-2959) in aqueous solution to form a hydrogel precursor composition for making the calcified-zone gel.

Step 2) Calcified-zone-specific IHH morphogen is encapsulated in nanogel/microcapsule composites with the desired delayed and duration of release, chondrogenic TGFβ1 morphogen is encapsulated in nanogel/microcapsule composites with the desired delayed and duration of release, and mesenchymal stem cells (chondroprogenitor cells) are suspended in the hydrogel precursor composition to form the calcified-zone precursor composition.

Step 3) The calcified-zone precursor composition is pipetted onto a Teflon or glass mold (thickness: the desired thickness for calcified zone of articular cartilage is between 100-500 μm) and irradiated with ultraviolet (UV) until the precursor composition reaches gelation point but is not fully crosslinked. The cell density in the gel can be varied from about 10 million to about 200 million cells/mL. The duration of IHH and TGFβ1 release can be varied from a few days to many weeks and the delay time can vary from a few days to a few weeks. The duration of IHH and TGFβ1 release can be 3 and 9 weeks, respectively in one embodiment. The delay time for the release of IHH may be six weeks and TGFβ1 may have no delay in release. The amount of TGFβ1 in the calcified-zone gel may be in the 10-100 ng/mL range and the amount of IHH may be in the 1-10 ng/m L range.

Step 4) The same hydrogel precursor composition as was used for the calcified-zone gel can be used for making the middle-zone gel.

Step 5) Middle-zone-specific IGF1 morphogen is encapsulated in nanogel/microcapsule composites with the desired delayed and duration of release, chondrogenic TGFβ1 morphogen is encapsulated in nanogel/microcapsule composites with the desired delayed and duration of release, and mesenchymal stem cells are suspended in the hydrogel precursor composition to form the middle-zone precursor solution.

Step 6) The middle-zone precursor composition is pipetted on top of the calcified-zone gel in the mold (thickness: the desired thickness for middle zone of articular cartilage between 100-1000 μm) and irradiated with ultraviolet (UV) until the precursor composition reaches gelation point but not fully crosslinked. The cell density in the gel can be varied from 15 million to about 150 million cells/mL. The duration of IGF1 and TGFβ1 release can be varied from a few days to many weeks and the delay time can vary from a few days to a few weeks. The duration of IGF1 and TGFβ1 may be 3 and 6 weeks, respectively. The delay time for the release of IGF1 may be three weeks and TGFβ1 may have no delay in release. The amount of TGFβ1 in the middle-zone gel may be in the 10-100 ng/mL range and the amount of IGF1 may be in the 100-1000 ng/m L range.

Step 7) The same hydrogel precursor composition as was used for the calcified-zone gel and the middle-zone gel can be used for making the superficial-zone gel.

Step 8) Superficial-zone-specific BMP7 morphogen is encapsulated in nanogel/microcapsule composites with the desired delayed and duration of release, chondrogenic TGFβ1 morphogen is encapsulated in nanogel/microcapsule composites with the desired delayed and duration of release, and mesenchymal stem cells are suspended in the hydrogel precursor composition to form the superficial-zone precursor composition.

Step 9) The superficial-zone precursor composition is pipetted on top of the calcified/middle-zones gel in the mold (thickness: the desired thickness for superficial zone of articular cartilage between 100-500 μm) and irradiated with ultraviolet (UV) until the precursor composition reaches gelation point but not fully crosslinked. The cell density in the gel can be varied from about 20 million to about 200 million cells/m L. The duration of BMP7 and TGFβ1 release can be varied from a few days to many weeks and the delay time can vary from a few days to a few weeks. The duration of BMP7 and TGFβ1 may be 3 and 3 weeks, respectively. The BMP7 and TGFβ1 in the superficial-zone layer may have no delay time. The amount of TGFβ1 in the superficial-zone gel may be in the 1-10 ng/mL range and the amount of BMP7 may be in the 100-1000 ng/m L range.

Step 10) The same hydrogel precursor composition as was used for each of the three layers can be used for dipping the multilayer hydrogel construct.

Step 11) The fetal-mimetic multilayer hydrogel construct consisting of calcified-, middle-, and superficial-zone gels is dipped in the hydrogel precursor solution and the multilayer is irradiated with UV to fully crosslink and fuse all layers into a pre-formed graft for implantation in a full-thickness articular cartilage defect.

Following formation of the multi-layer structure, a multilayer graft can be inserted in a defect as an implantable graft. Following implantation, the microcapsules of each layer 63, 73, 83 can degrade according to the predetermined release profiles, which, in turn, can release the nanogels contained therein and allow for the sustained release of the signaling molecules contained in the nanogels. For example, TGFβ1-conjugated nanogel/microcapsules present in one or more layers can begin to degrade relatively quickly following formation with the nanogels releasing the TGFβ1 over the entire course of a tissue formation protocol (e.g., weeks 1-9), which can stimulate condensation of the MSCs contained in the multilayer structure 60. BMP7-conjugated nanogel/microcapsules present in the first layer 63 can also begin to degrade relatively quickly following formation, and these nanogels can release the BMP7 over weeks 1-3 of the tissue formation protocol. The release of the BMP7 in conjunction with the TGFβ1 can encourage chondrogenic differentiation of the MSCs to form a matrix similar to the superficial zone of articular cartilage. IGF1-conjugated nanogel/microcapsules present in the second layer 73 can begin to degrade following the predetermined delay period so as to release the IGF1 over weeks 4-6 of the tissue formation protocol leading to the development of two distinct superficial 66 and middle zones 76 and the further differentiation of pre-chondrocytes to pre-hypertrophic chondrocytes. Release of IHH from the IHH-conjugated nanogel/microcapsules in the third layer 83 following the predetermined delay period over weeks 7-9 of the tissue formation can lead to complete zonal organization of articular cartilage including superficial zone 66, the middle zone 76, and the calcified zone 86.

Thus, the combination of delayed and sustained release of the signaling molecules in the composition can provide for in situ differentiation and maturation of cells that are either in the local area of the composition or contained in the composition itself so as to provide improved tissue generation and healing.

The present disclosure may be better understood with reference to the Examples set forth below.

EXAMPLE

Articular cartilage is structurally composed of multiple zones with distinct functions including the superficial zone for joint lubrication, middle zone for compressive strength, and calcified zone for load transfer to the underlying bone tissue. The superficial zone is characterized by pre-chondrocytes with high expression of superficial zone protein (SZP) for joint lubrication. The middle zone is characterized by pre-hypertrophic chondrocytes with high expression of glycosaminoglycans (GAG) and aggrecans (AGCs) for compressive strength. The calcified zone is characterized by hypertrophic chondrocytes with high expression of collagen type X (Col X) and alkaline phosphatase (ALP) for the formation of a mineralized matrix.

Figure 4:
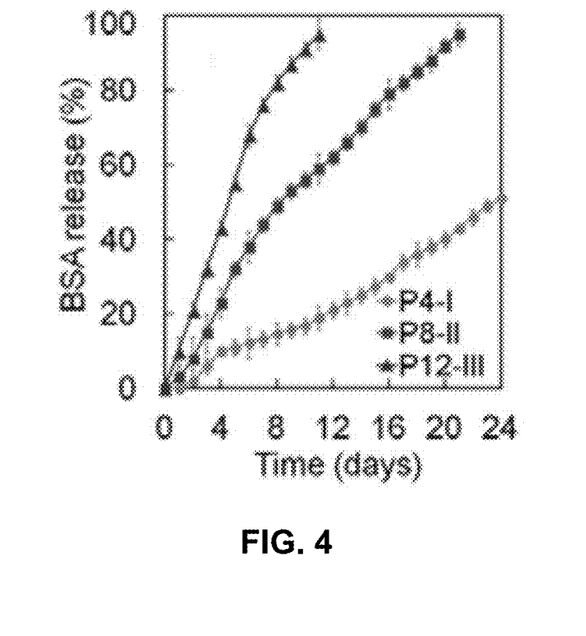
FIG. 4 graphically illustrates the effect of polymer molecular weight on the release rate for a protein conjugated to the polymer of a nanogel.
Figure 5:
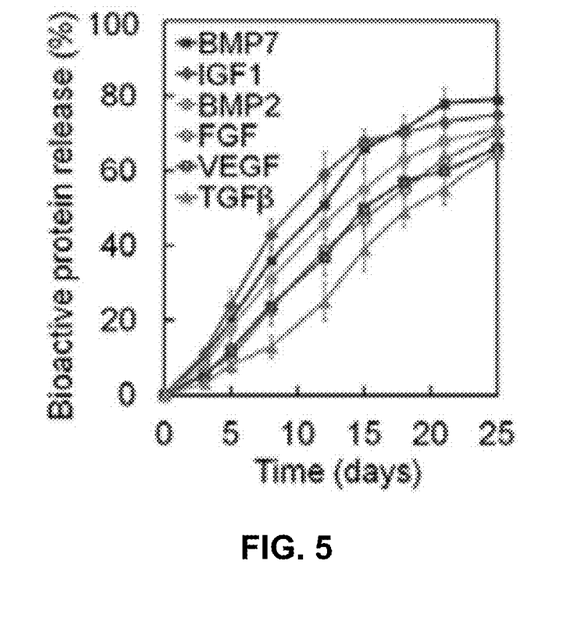
FIG. 5 presents the release kinetics of six different proteins from nanogels as described herein.
Figure 6:
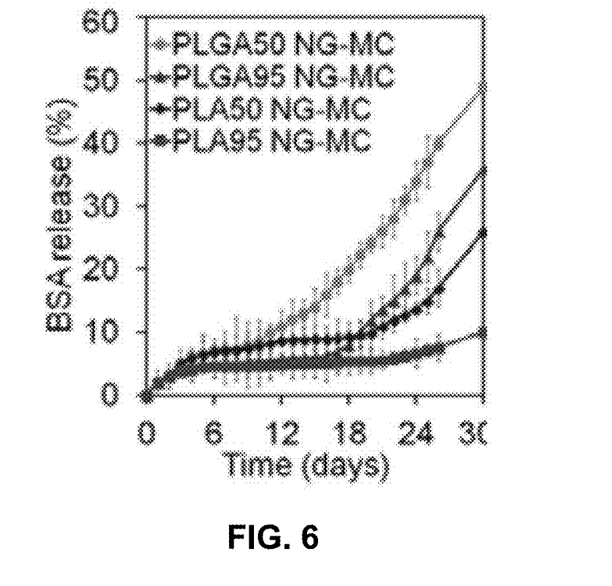
FIG. 6 illustrates the effect of modification in polymer/emulsifying agent concentration used in the formation of microcapsules on the delay time prior to release of protein from nanogels encapsulated within the microcapsules.

It has been demonstrated that proteins can be conjugated with high efficiency to nanogels based on polyethylene oxide macromers chain-extended with short lactide-glycolide segments (PEG-sLG) and the protein can be released with high bioactivity and at a prescribed rate. FIG. 4 shows that the release rate and duration of bovine serum albumin (BSA) conjugated to PEG-sLG nanogels can be controlled by changing the PEG molecular weight (P4-I—4 kDa PEG, P8-II—8 kDa PEG, P12-III—12 kDa PEG). FIG. 5 shows that different proteins (BMP7, BMP2, IGF1, TGFβ1, FGF, VEGF) conjugated to PEG-sLG nanogels are released at a prescribed rate with >60% bioactivity. FIG. 6 shows that BSA-conjugated nanogels produced from acrylated PEG-sLG (PEG-sLG-Ac) and further encapsulated in PLGA microcapsules (NG-MCs) release the protein after a predefined delay time ranging from a few days to 20 days, depending upon the polymer type and the PLEOF emulsifier concentration (PLGA50—PLGA copolymer using 50:50 wt. % PLGA:PLEOF in the organic phase; PLGA95—PLGA copolymer using 95:5 wt. % PLGA:PLEOF in the organic phase; PLA50—PLA homopolymer using 50:50 wt. % PLA:PLEOF in the organic phase; PLA95—PLA homopolymer using 95:5 wt. % PLA:PLEOF in the organic phase).

Figure 7:
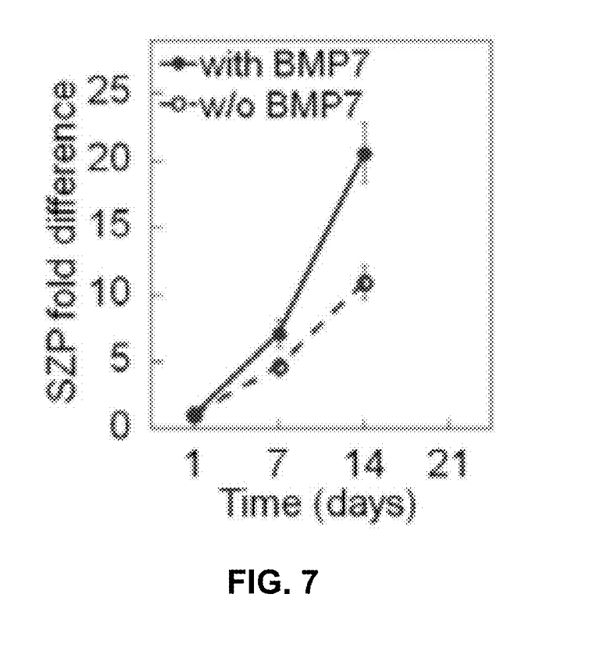
FIG. 7 illustrates the effect of TGFβ1/BMP7 release with incubation time on the expression of the cartilage superficial zone marker SZP from mesenchymal stem cells.
Figure 8:
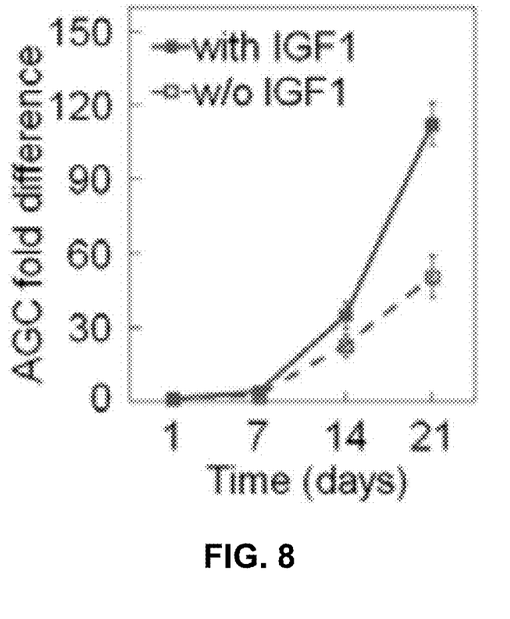
FIG. 8 illustrates the effect of TGFβ1/IGF1 release with incubation time on the expression of the cartilage middle zone marker AGC from mesenchymal stem cells.
Figure 9:
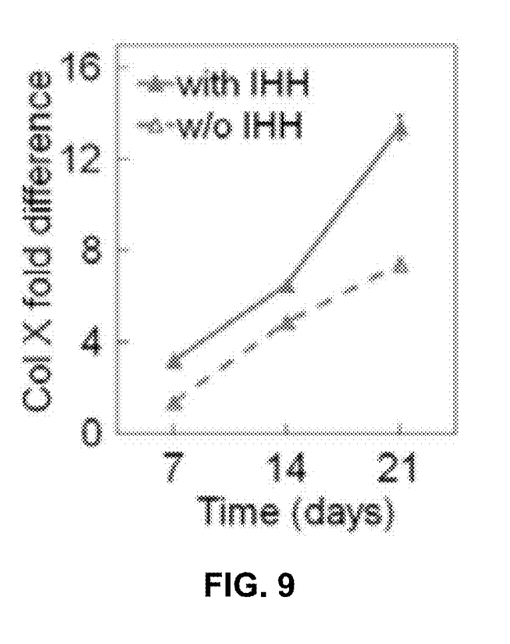
FIG. 9 illustrates the effect of TGFβ1/IHH release with incubation time on the presence of Col X in mesenchymal stem cells.

The combination of TGFβ1 and BMP7 stimulates chondrogenic differentiation of encapsulated mesenchymal stem cells to the superficial zone phenotype (FIG. 7); the combination of TGFβ1 and IGF1 stimulates the middle zone phenotype (FIG. 8); the combination of TGFβ1 and IHH stimulates the calcified zone phenotype (FIG. 9).

Figure 10:
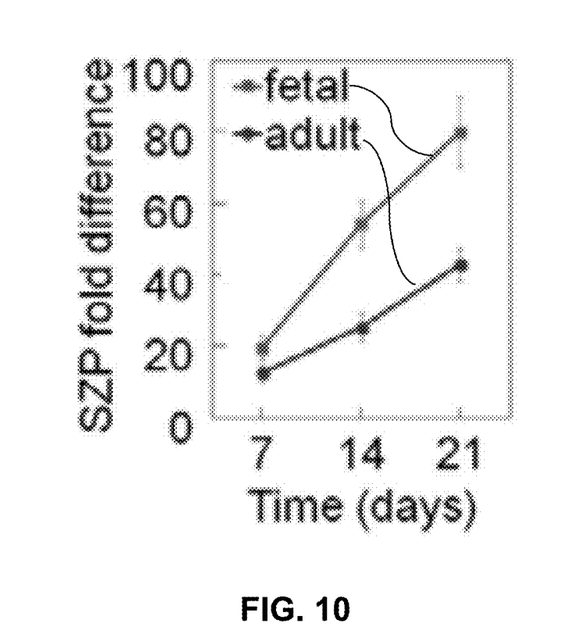
FIG. 10 compares a matrix based upon digested fetal articular cartilage with a matrix based upon digested adult articular cartilage with regard to the difference in the cartilage superficial zone marker SZP.
Figure 11:
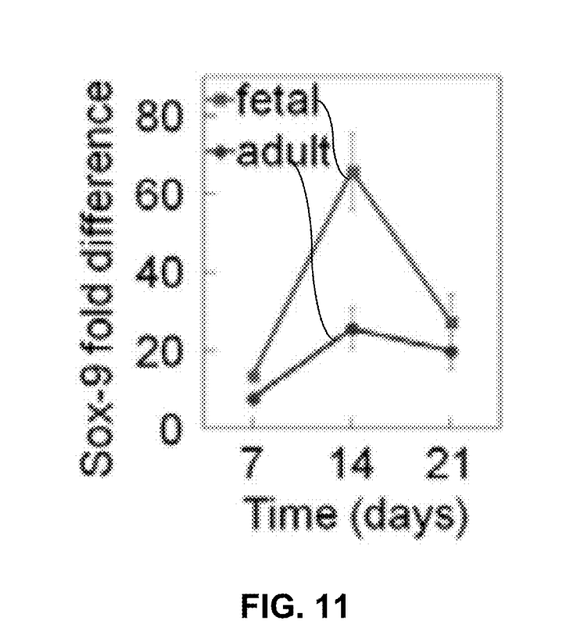
FIG. 11 compares a matrix based upon digested fetal articular cartilage with a matrix based upon digested adult articular cartilage with regard to the difference in the prechondrogenic marker Sox 9.
Figure 12:
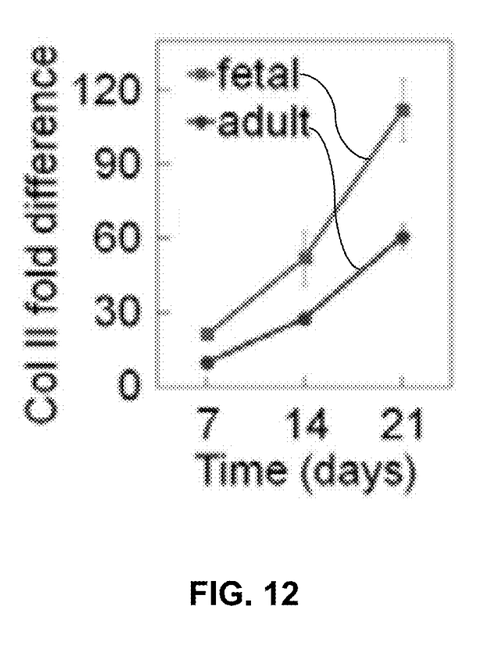
FIG. 12 compares a matrix based upon digested fetal articular cartilage with a matrix based upon digested adult articular cartilage with regard to the difference in the quantity of Col II.

Encapsulation of mesenchymal stem cells in a hydrogel based on digested bovine fetal articular cartilage and cultivation in chondrogenic medium supplemented with BMP7 sharply enhanced stem cell differentiation to the superficial zone phenotype compared to that of adult articular cartilage (FIG. 10, FIG. 11, FIG. 12). As shown, human MSCs encapsulated in digested fetal bovine articular cartilage and cultured in chondrogenic medium have higher expression of pre-chondrogenic markers Sox-9 (FIG. 11) and superficial zone protein (SZP) (FIG. 10) and collagen type II (Col II; FIG. 12) compared to those of adult cartilage.

These results support in situ zonal regeneration of articular cartilage by sequential/sustained release of zone-specific morphogens in an injectable fetal articular cartilage-derived matrix.

While certain embodiments of the disclosed subject matter have been described using specific terms, such description is for illustrative purposes only, and it is to be understood that changes and variations may be made without departing from the spirit or scope of the subject matter.

What is claimed is:

1. A multi-layered articular cartilage implant comprising:
    a first crosslinked hydrogel layer including a plurality of first nanogels, each first nanogel including a first crosslinked degradable polymer conjugated to bone morphogenetic protein (BMP7), the first crosslinked layer further comprising a plurality of first microcapsules, each first microcapsule carrying a plurality of the first nanogels, the first microcapsules each comprising a shell that includes a first bioerodable polymer;
    a second crosslinked hydrogel layer including a plurality of second nanogels, each second nanogel including a second crosslinked degradable polymer conjugated to insulin-like growth factor-1 (IGF1), the second crosslinked layer further comprising a plurality of second microcapsules, each second microcapsule carrying a plurality of the second nanogels, the second microcapsules each comprising a shell that includes a second bioerodable polymer; and
    a third crosslinked hydrogel layer including a plurality of third nanogels, each third nanogel including a third crosslinked degradable polymer conjugated to Indian Hedgehog (IHH), the third crosslinked layer further comprising a plurality of third microcapsules, each third microcapsule carrying a plurality of the third nanogels, the third microcapsules each comprising a shell that includes a third bioerodable polymer.

2. The implant of claim 1, further comprising transforming growth factor-β1 (TGFβ1) in one or more of the hydrogel layers.

3. The implant of claim 1, further comprising cells in one or more of the layers.

4. The implant of claim 1, wherein the first, second, and third crosslinked degradable polymers comprise first, second, and third polyethylene glycol polymers, respectively.

5. The implant of claim 1, wherein the first, second, and third bioerodable polymers comprise first, second, and third polylactide polymers, respectively.

6. The implant of claim 1, wherein each of the first, second, and third hydrogels comprise a crosslinked biopolymer.

7. The implant of claim 6, wherein the crosslinked biopolymer is derived from articular cartilage.

8. A method for forming a multi-layered articular cartilage implant comprising:
    forming a first composition comprising a plurality of first nanogels, each first nanogel including a first crosslinked degradable polymer conjugated to BMP7, the first composition further comprising a plurality of first microcapsules, each first microcapsule carrying a plurality of the first nanogels, the first microcapsules each comprising a shell that includes a first bioerodable polymer;
    partially crosslinking the first composition to form a first layer;
    placing a second composition on a surface of the first layer, the second composition comprising a plurality of second nanogels, each second nanogel including a second crosslinked degradable polymer conjugated to IGF1, the second composition further comprising a plurality of second microcapsules, each second microcapsule carrying a plurality of the second nanogels, the second microcapsules each comprising a shell that includes a second bioerodable polymer;
    partially crosslinking the second composition to form a second layer;
    placing a third composition on a surface of the second layer, the third composition including a plurality of third nanogels, each third nanogel including a third crosslinked degradable polymer conjugated to IHH, the third composition further comprising a plurality of third microcapsules, each third microcapsule carrying a plurality of the third nanogels, the third microcapsules each comprising a shell that includes a third bioerodable polymer; and
    crosslinking the third layer.

9. The method of claim 8, further comprising incorporating TGFβ1 into one or more of the first, second, and third layers.

10. The method of claim 8, further comprising incorporating cells in one or more of the layers.

* * * * *